United States Patent
Lund et al.

(10) Patent No.: US 11,807,643 B2
(45) Date of Patent: Nov. 7, 2023

(54) FLUORESCENT DYES

(71) Applicant: Cepheid, Sunnyvale, CA (US)

(72) Inventors: Kevin P. Lund, Sunnyvale, CA (US);
Dmitri Sergueev, Sunnyvale, CA (US);
Alexander Gall, Sunnyvale, CA (US)

(73) Assignee: Cepheid, Sunnyvale, CA (US)

( * ) Notice: Subject to any disclaimer, the term of this patent is extended or adjusted under 35 U.S.C. 154(b) by 190 days.

(21) Appl. No.: 17/374,514

(22) Filed: Jul. 13, 2021

(65) Prior Publication Data

US 2022/0017531 A1     Jan. 20, 2022

Related U.S. Application Data

(60) Provisional application No. 63/052,862, filed on Jul. 16, 2020.

(51) Int. Cl.
*C07D 491/052* (2006.01)
*C09B 11/24* (2006.01)
*C12Q 1/686* (2018.01)

(52) U.S. Cl.
CPC .......... *C07D 491/052* (2013.01); *C09B 11/24* (2013.01); *C12Q 1/686* (2013.01)

(58) Field of Classification Search
CPC ...... C07D 491/052; C09B 11/24; C12Q 1/686
See application file for complete search history.

(56) References Cited

FOREIGN PATENT DOCUMENTS

| WO | 2005/102176 A1 | 11/2005 |
| WO | 2019/217470 A1 | 11/2019 |

OTHER PUBLICATIONS

International Search Report and Written Opinion dated Oct. 14, 2021, issued in corresponding International Application No. PCT/US2021/041416, filed Jul. 16, 2021, 10 pages.

*Primary Examiner* — Bruck Kifle
(74) *Attorney, Agent, or Firm* — Christensen O'Connor Johnson Kindness PLLC

(57) ABSTRACT

Automated oligonucleotide synthesis-compatible fluorescent dye phosphoramidite compounds, solid supports, and labeled polynucleotides incorporating the compounds are provided. The compounds allow universal incorporation of the fluorescent label into any position of the polynucleotide.

36 Claims, No Drawings

FLUORESCENT DYES

CROSS-REFERENCE TO RELATED APPLICATION

This application claims the benefit of U.S. Application No. 63/052,862, filed Jul. 16, 2020, expressly incorporated herein by reference in its entirety.

BACKGROUND OF THE INVENTION

Fluorescent dyes are among the most commonly used tags for modifying oligonucleotides because they offer sensitive detection in a wide variety of applications ranging from PCR to sequencing. Preparation of fluorescent dye-labeled polynucleotides is typically done by post-synthetic conjugation, for example, by reacting an activated dye intermediate with an amino derivative of a polynucleotide. This approach suffers from certain drawbacks, including low conjugation yields and the need for additional purification of the conjugated product. Incorporation of fluorescent dyes into synthetic polynucleotides via automated phosphoramidite synthesis offers a more convenient approach. However, few phosphoramidite derivatives of fluorescent dyes which allow the fluorescent dye to be added to the polynucleotide as part of the automated solid phase synthesis are commercially available. Moreover, few such derivatives exist that can allow incorporation of fluorescent dye moiety at any position of a synthetic polynucleotide.

Thus, a need still exists for fluorescent dyes that are compatible with the conditions of automated phosphoramidite oligonucleotide synthesis, can be incorporated into any position of a polynucleotide, and provide a high end-point fluorescence signal in PCR applications.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides a compound represented by Formula I:

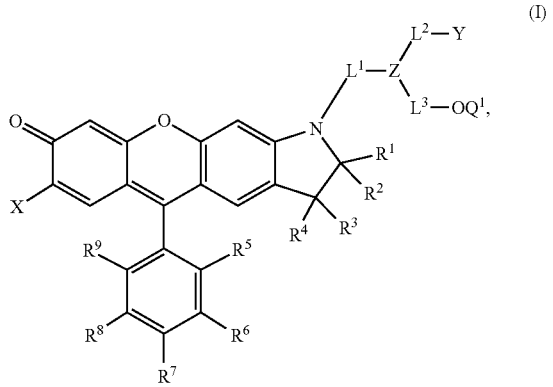

(I)

or a stereoisomer, a salt, or a tautomer thereof, wherein:
X is H, halogen, or $C_1$-$C_5$ alkyl; $R^1$, $R^2$, $R^3$, and $R^4$ are independently H or optionally substituted $C_1$-$C_6$ alkyl; $R^5$, $R^6$, $R^7$, $R^8$, and $R^9$ are independently H, halogen, or optionally substituted $C_1$-$C_6$ alkyl; $L^1$ is an optionally substituted $C_2$-$C_{10}$ alkylene or optionally substituted $C_2$-$C_{50}$ heteroalkylene; $L^2$ and $L^3$ are independently an optionally substituted $C_2$-$C_{10}$ alkylene or optionally substituted $C_2$-$C_{30}$ heteroalkylene; $Q^1$ is a hydroxyl protecting group; Z is CH, N, NHC(O)N, or OC(O)N; Y is OH, OP(OCH$_2$CH$_2$CN)NR$^{10}$R$^{11}$, or a solid support; and $R^{10}$ and $R^{11}$ are independently optionally substituted $C_1$-$C_6$ alkyl.

In some embodiments, X is Cl, Br, or F. In some embodiments, X is Cl. In some embodiments, X is F. In some embodiments, X is optionally substituted methyl or optionally substituted ethyl. In some embodiments, X is o-MeC$_6$H$_4$CH$_2$.

In some embodiments, the solid support is controlled pore glass or polystyrene.

In some embodiments, the compound is compound of formula (IA):

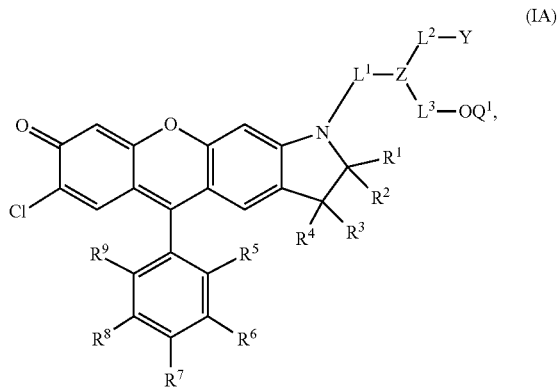

(IA)

or a stereoisomer, a salt, or a tautomer thereof.

In some embodiments, $R^1$ is H. In some embodiments, $R^2$ is methyl. In some embodiments, $R^3$ is methyl. In some embodiments, $R^4$ is methyl. In some embodiments, the compound is a compound of formula (IB):

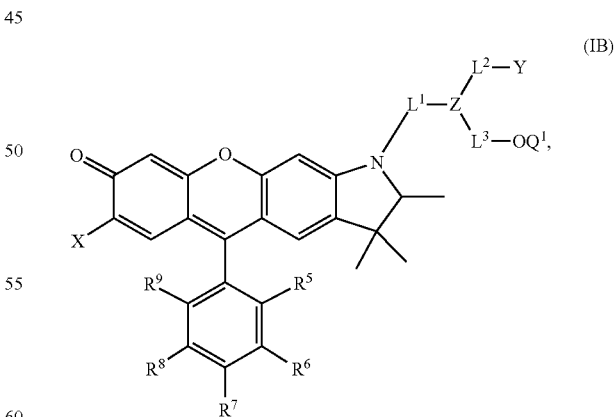

(IB)

or a stereoisomer, a salt, or a tautomer thereof.

In some embodiments, $L^1$ is $C_2$-$C_6$ alkylene or —(CH$_2$CH$_2$O)$_m$CH$_2$CH$_2$—, wherein m is an integer from 1 to 10. In some embodiments, $L^1$ is $C_2$ alkylene. In some embodiments, Z is OC(O)N.

In some embodiments, the compound is a compound of formula (IC):

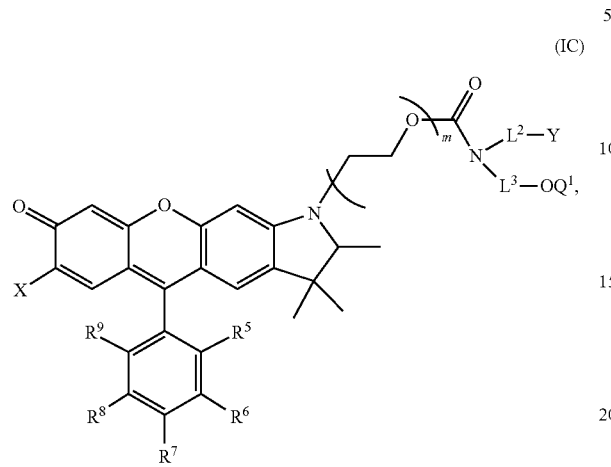

(IC)

or a stereoisomer, a salt, or a tautomer thereof, wherein m is an integer from 1 to 10.

In some embodiments, compound is a compound of formula (ID):

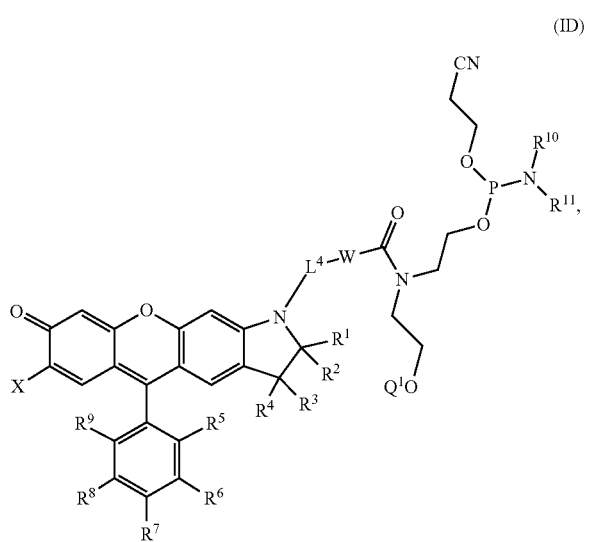

(ID)

or a stereoisomer, a salt, or a tautomer thereof, wherein W is NH or O, and $L^4$ is an optionally substituted $C_2$-$C_{10}$ alkylene or optionally substituted $C_2$-$C_{50}$ heteroalkylene.

In some embodiments, $Q^1$ is trimethylsilyl, TBDMS, acetyl, dimethoxy trityl, or trityl. In some embodiments, $R^{10}$ and $R^{11}$ are isopropyl. In some embodiments, $R^5$ is methyl. In some embodiments, $R^7$ is methyl. In some embodiments, $R^8$ is methyl. In some embodiments, $R^6$ and $R^9$ are H.

In some embodiments, the compound is a compound of formula (IE):

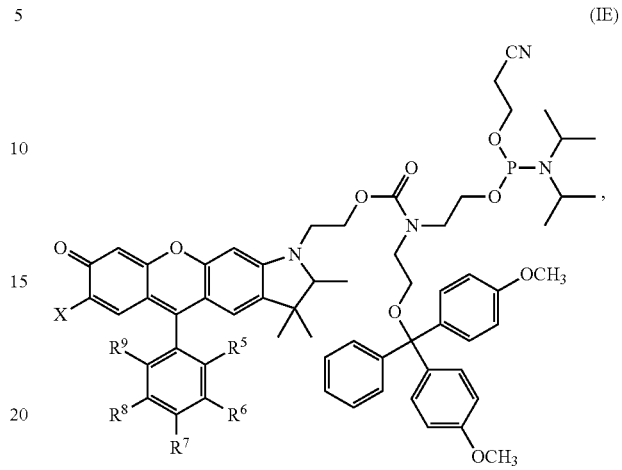

(IE)

or a stereoisomer, a salt, or a tautomer thereof.

In another aspect, the disclosure provides a labeled polynucleotide comprising the residue of a compound of the disclosure. In some embodiments, the labeled polynucleotide is prepared using automated phosphoramidite synthesis. In some embodiments, the labeled polynucleotide further comprises a fluorescence quencher. In some embodiments, the labeled polynucleotide further comprises a BHQ type fluorescence quencher. In some embodiments, the labeled polynucleotide is attached to a solid support. In some embodiments, the solid support is a controlled pore glass bead, polystyrene bead, magnetic bead, or microwell plate.

In another aspect, the disclosure provides a method for preparing a labeled conjugate of a ligand comprising contacting a ligand with a compound of any one of claim 1 to claim 22, wherein Y is OP(OCH$_2$CH$_2$CN)NR$^{10}$R$^{11}$ and R$^{10}$ and R$^{11}$ are independently optionally substituted $C_1$-$C_6$ alkyl, in a suitable solvent under conditions sufficient to covalently attach the compound to the ligand thereby forming the labeled conjugate.

In some embodiments, the ligand is a polynucleotide or a solid support. In some embodiments, the ligand is a polynucleotide. In some embodiments, the conditions sufficient to covalently attach the compound to the ligand are automated phosphoramidite oligonucleotide synthesis conditions.

In another aspect, the disclosure provides a kit comprising the labeled polynucleotide disclosed herein, such as a PCR diagnostic kit.

DETAILED DESCRIPTION

Provided herein are fluorescent dye derivatives, such as phosphoramidites, that can be incorporated into oligonucleotides via standard automated oligonucleotide synthesis. Solid supports modified with the fluorescent dyes and polynucleotides comprising the fluorescent dyes are also provided.

Throughout the present specification and the accompanying claims, the words "comprise" and "include" and variations thereof such as "comprises," "comprising," "includes," and "including" are intended to convey the possible inclusion of other elements or integers not specifically recited, where the context allows. As used herein, the term "consisting of" is intended to mean including and limited to whatever follows the phrase "consisting of." Thus, the phrase "consisting of" indicates that the listed elements are required or mandatory and that no other elements may be present. The term "consisting essentially or means that the composition, method or structure may include additional ingredients, steps and/or parts, but only if" the additional ingredients, steps and/or parts do not materially alter the basic and novel characteristics of the claimed composition, method or structure.

The terms "a" and "an" and "the" and similar terms are to be construed to cover both the singular and the plural, unless otherwise indicated herein or clearly contradicted by context.

All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise indicated, nucleic acids or oligonucleotides are written left to right in 5' to 3' orientation.

As used herein, the term "amplification" refers to any means by which at least a partial sequence of at least one target nucleic acid or its sequence complement is produced, typically in a template-dependent manner, including without limitation, a broad range of techniques for amplifying nucleic acid sequences, either linearly or exponentially. Non-limiting exemplary amplification methods include polymerase chain reaction (PCR), reverse-transcriptase PCR, real-time PCR, nested PCR, multiplex PCR, quantitative PCR (Q-PCR), nucleic acid sequence based amplification (NASBA), transcription mediated amplification (TMA), ligase chain reaction (LCR), rolling circle amplification (RCA), strand displacement amplification (SDA), ligase detection reaction (LDR), multiplex ligation-dependent probe amplification (MLPA), ligation followed by Q-replicase amplification, primer extension, strand displacement amplification (SDA), hyperbranched strand displacement amplification, multiple displacement amplification (MDA), nucleic acid strand-based amplification (NASBA), two-step multiplexed amplifications, digital amplification, and the like. Descriptions of such techniques can be found in, among other sources, Ausubel et al.; PCR Primer: A Laboratory Manual, Diffenbach, Ed., Cold Spring Harbor Press (1995); The Electronic Protocol Book, Chang Bioscience (2002); The Nucleic Acid Protocols Handbook, R. Rapley, ed., Humana Press, Totowa, N.J. (2002); and Innis et al, PCR Protocols: A Guide to Methods and Applications, Academic Press (1990).

As used herein, the term "base" means a nitrogen-containing heterocyclic moiety capable of forming hydrogen bonds, e.g., Watson-Crick type hydrogen bonds, with a complementary nucleotide base or nucleotide base analog, e.g. a purine, a 7-deazapurine, or a pyrimidine. Typical bases are the naturally occurring bases adenine, cytosine, guanine, thymine, and uracil. Bases also include analogs of naturally occurring bases such as deazaadenine, 7-deaza-8-azaadenine, 7-deazaguanine, 7-deaza-8-azaguanine, inosine, nebularine, nitropyrrole, nitroindole, 2-amino-purine, 2,6-diamino-purine, hypoxanthine, 5-methylcytosine, isocytosine, pseudoisocytosine, 5-bromouracil, 5-propynyluracil, 6-aminopurine, 2-chloro-6-aminopurine, xanthine, hypoxanthine, etc.

As used herein, the term "complementary" refers to the ability of polynucleotide sequences to hybridize to and from base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. The percentage of "complementarity" of a probe sequence to a target sequence is the percentage "identity" of the probe sequence to the sequence of the target or to the complement of the sequence of the target. In determining the degree of "complementarity" between a probe and a target sequence, the degree of "complementarity" is expressed as the percentage identity between the sequence of the probe and the sequence of the target sequence or the complement of the sequence of the target sequence that best aligns therewith. An exemplary probe is a polynucleotide as described herein.

As used herein, the term "duplex" refers to a double-stranded hybridization complex formed by annealing (hybridizing) complementary (or partially complementary) single-stranded polynucleotides, e.g., DNA, RNA, LNA, or peptide nucleic acid (PNA).

As used herein, "fluorescence quenching" refers to any process that decreases the fluorescence intensity of a fluorescent sample, i.e., a fluorescent polynucleotide probe. A variety of molecular interactions can result in quenching. Non-limiting examples include excited-state reactions, molecular rearrangements, energy transfer, ground-state complex formation, and collisional quenching.

As used herein, "halogen" means F, Cl, Br, or I.

The terms "hybridize" and "hybridization" are used herein with reference to "specific hybridization" which is the binding, duplexing, or annealing of a nucleic acid molecule preferentially to a particular nucleotide sequence, in some embodiments, under stringent conditions. The term "stringent conditions" refers to conditions under which a probe will hybridize preferentially to its target sequence, and to a lesser extent to, or not at all to, other sequences. "Stringent hybridization" and "stringent hybridization wash conditions" in the context of nucleic acid hybridization are sequence-dependent and are different under different environmental parameters. An extensive guide to the hybridization of nucleic acids is found in, e.g., Tijssen (1993) Laboratory Techniques in Biochemistry and Molecular Biology-Hybridization with Nucleic Acid Probes part I, Ch. 2, "Overview of principles of hybridization and the strategy of nucleic acid probe assays," Elsevier, NY. The degree of hybridization of a polynucleotide to a target sequence, also known as hybridization strength, is determined by methods that are well-known in the art. A preferred method is to determine the $T_m$ of a given hybrid duplex. This can be accomplished by subjecting a formed duplex in solution to gradually increasing temperature and monitoring the denaturation of the duplex, for example, by absorbance of ultraviolet light, which increases with the unstacking of base pairs that accompanies denaturation. $T_m$ is generally defined as the temperature at which half of the DNA strands are in the single-stranded (ssDNA) state. $T_m$ depends on various parameters such as the length of the hybridized complementary strand sequence, their specific nucleotide sequences, base compositions, base modifications, and the concentrations of the complementary strands.

As used herein, the terms "label" and "detectable label" are used interchangeably and refer to a moiety that, when attached to a biomolecule, a nucleoside, a nucleotide, or a polynucleotide, renders such biomolecule, nucleoside, nucleotide, or polynucleotide detectable by suitable detection means. Exemplary labels include fluorophores, chromophores, radioisotopes, spin-labels, enzyme labels, chemiluminescent labels, electrochemiluminescent compounds, magnetic labels, microspheres, colloidal metal, immunologic labels, ligands, enzymes, and the like.

As used herein, the terms "modified nucleotide base" or "modified base" refer to a base that does not have the structure of a naturally occurring base and thus, is non-naturally occurring. As used herein, the terms "modified sugar" refers to a sugar or sugar analog that does not have the structure of a naturally occurring sugar, e.g. ribose or deoxyribose sugar, and thus is non-naturally occurring.

As used herein, the term "naturally-occurring" in the context of nucleic acid molecules refers to an RNA or DNA molecule (single-stranded or double-stranded) having a nucleotide sequence that occurs in nature and comprising only components, such as bases, sugars, nucleosides, and nucleotides that occur in nature.

As used herein, the term "nucleoside" refers to a molecule consisting of a nitrogenous base of the type mentioned herein that is bound to a sugar of the types mentioned herein, for example, to ribose or deoxyribose sugar via a beta-glycosidic linkage. Examples of nucleosides include adenosine, cytidine, guanosine, thymidine, uridine, and inosine.

As used herein, the term "nucleotide" means a phosphate ester of a nucleoside, either as an independent monomer or as a subunit within a polynucleotide. Nucleotide monomers include for example nucleotide 5'-monophosphate, 5'-diphosphate, 5'-triphosphate, and 3'-monophosphate. Nucleotide triphosphates are sometimes denoted as "NTP", "dNTP" (2'-deoxypentose) or "ddNTP" (2', 3'-dideoxypentose) to particularly point out the structural features of the ribose sugar. "Nucleotide 5'-triphosphate" refers to a nucleotide with a triphosphate ester group at the 5' position. The triphosphate ester group may include sulfur substitutions for one or more phosphate oxygen atoms, e.g. alpha-thionucleotide 5'-triphosphates. A nucleotide monophosphate, diphosphate or triphosphate may serve as the substrate for a nucleic acid processing enzyme that catalyzes modifications of nucleic acids or nucleic acid intermediates.

As used herein, the term "oligonucleotide" broadly refers to a single stranded chain composed primarily or entirely of about 2 to about 300 naturally occurring or modified nucleotide monomer units, e.g., of deoxyribose or ribose sugar rings substituted with A, C, G, T, or U bases and which are linked by conventional phosphate backbone moieties. More particularly, the term refers to a single stranded chain of deoxyribonucleotides, in the size range described above. In some embodiments, an oligonucleotide can comprise one or more modified bases and/or sugars. In addition to nucleotide monomer units, an oligonucleotide can incorporate one or more detectable labels and/or one or more reactive groups.

As used herein, the term "plurality" means more than one.

As used herein, the term "polynucleotide" generally refers to an oligonucleotide that comprises about 10 to about 300 nucleotide monomer units. In addition to nucleotide monomer units, a polynucleotide can incorporate one or more detectable labels and/or one or more reactive groups.

As used herein, the term "primer" refers to a polynucleotide or modified polynucleotide that is effective as a starting point to synthesize a polynucleotide strand that is complementary to a target nucleic acid strand. For example, primers for use in PCR comprise a forward and reverse primer wherein the forward primer contains a sequence complementary to a region of a target nucleic acid strand and guides synthesis of a complementary strand. A reverse primer contains a sequence complementary to the opposite stand and guides synthesis along the opposite strand of the target nucleic acid strand.

As used herein, the term "probe" refers to a labeled oligonucleotide or labeled modified oligonucleotide containing a sequence complementary to a region of a target nucleic acid sequence, allowing the probe to form a duplex with the target sequence and generate a detectable signal indicating the presence of the region of the target sequence. A detectable signal is generated during or after hybridization, either directly or indirectly. In some applications, such as during primer extension in 5'-nuclease PCR, the probes lack an extendable 3' hydroxyl group to prevent polymerase-mediated extension of the probe. In certain embodiments, probes include TaqMan® probes, TaqMan MGB® probes, Pleiades® probes, molecular beacons (e.g., those disclosed in Tyagi, Sanjay & Kramer, Fred. (2012) Molecular Beacons in Diagnostics. F1000 medicine reports. 4. 10. 10.3410/M4-10), and the like.

As used herein, the terms "protecting group," "protective group", or "protected form" refer to a labile chemical modification of a functional group (e.g., hydroxyl) meant to preserve its functionality and/or to obtain chemoselectivity in a subsequent chemical reaction. A protecting group is removed from the final product by a deprotective treatment (e.g., treatment with acid).

As used herein, the term "solid support" refers to any insoluble material including particles (e.g., beads), fibers, monoliths, membranes, filters, plastic strips, arrays, microwell plates, and the like. In some embodiments, solid supports are solid supports suitable for automated phosphoramidite oligonucleotide synthesis, such as polystyrene and controlled pore glass (CPG).

In one aspect, provided herein is a fluorescent dye compound represented by Formula I:

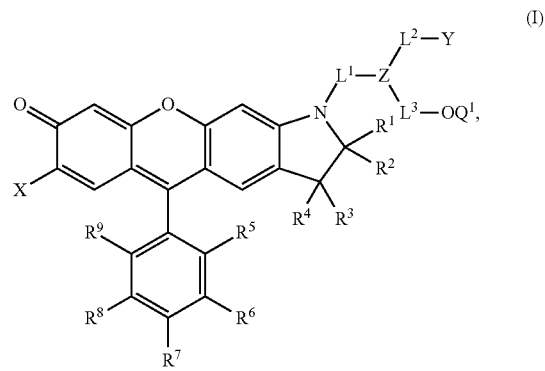

or a stereoisomer, a salt, or a tautomer thereof, wherein:

X is H, halogen, or an optionally substituted $C_1$-$C_5$ alkyl;

$R^1$, $R^2$, $R^3$, and $R^4$ are independently H or optionally substituted $C_1$-$C_6$ alkyl;

$R^5$, $R^6$, $R^7$, $R^8$, and $R^9$ are independently H, halogen, or optionally substituted $C_1$-$C_6$ alkyl;

$L^1$ is a linker group selected from an optionally substituted $C_2$-$C_{10}$ alkylene and optionally substituted $C_2$-$C_{50}$ heteroalkylene;

$L^2$ and $L^3$ are independently a linker group selected from an optionally substituted $C_2$-$C_{10}$ alkylene or optionally substituted $C_2$-$C_{30}$ heteroalkylene;

$Q^1$ is a hydroxyl protecting group, such as a compatible with automated oligonucleotide synthesis protective group;

Z is CH, N, NHC(O)N, or OC(O)N;

Y is OH, OP(OCH$_2$CH$_2$CN)NR$^{10}$R$^{11}$, or a solid support; and $R^{10}$ and $R^{11}$ are independently optionally substituted C1-C6 alkyl.

In some embodiments, Formula I comprises a phosphoramidite group (i.e., Y is OP(OCH$_2$CH$_2$CN)NR$^{10}$R$^{11}$) and a hydroxyl group protected with an acid-labile protective group, such as trityl or dimethoxytrityl group. In some embodiments, $Q^1$ is dimethoxytrityl group. In some embodiments, $R^{10}$ and $R^{11}$ are isopropyl.

In some embodiments of Formula I, X is Cl, Br, or F. In some embodiments, X is Cl.

In some embodiments, the compound is compound of formula (IA):

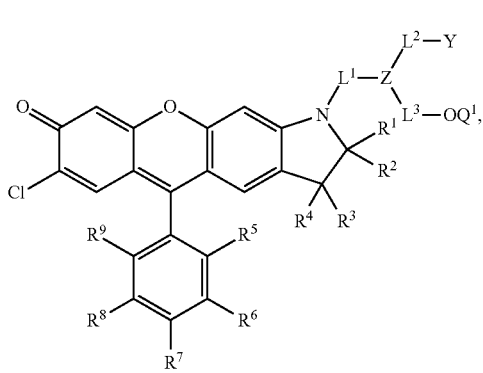

or a stereoisomer, a salt, or a tautomer thereof.

In some embodiments, $R^1$ is H. In some embodiments, $R^2$ is methyl. In some embodiments, $R^3$ is methyl. In some embodiments, $R^4$ is methyl. In some embodiments, $R^1$ is H, and each of $R^2$, $R^3$, and $R^4$ is methyl.

In some embodiments of Formula (I), the compound is a compound of formula (IB):

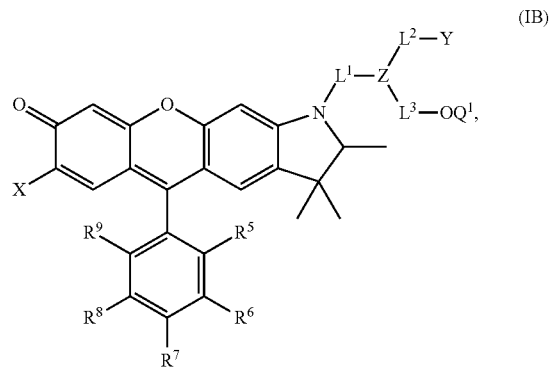

or a stereoisomer, a salt, or a tautomer thereof.

In the formulae disclosed herein, linker group $L^1$ can comprise one or more heteroatoms selected from N, O, S, P, and combinations thereof. In some embodiments, $L^1$ is a PEG$_{2-10}$ linker. In some embodiments, $L^1$ is a $C_2$-$C_6$ alkylene or —(CH$_2$CH2O)$_m$CH$_2$CH$_2$—, wherein m is an integer from 1 to 10. In other embodiments, $L^1$ is an optionally substituted alkylene, such as —CH$_2$CH$_2$—. In some embodiments, $L^1$ is an alkylene optionally substituted with a methyl group.

In some embodiments, Z is OC(O)N.

In some embodiments of Formulae (I), (IA), and (IB), the compound is a compound of formula (IC):

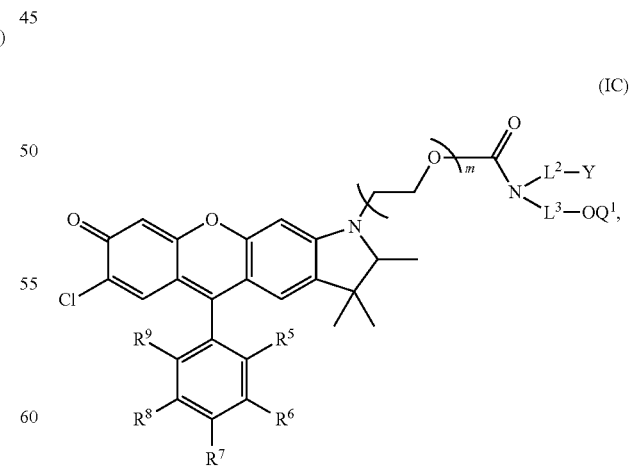

or a stereoisomer, a salt, or a tautomer thereof, wherein m is an integer from 1 to 10.

In some embodiments of Formulae (I), the compound is a compound of formula (ID):

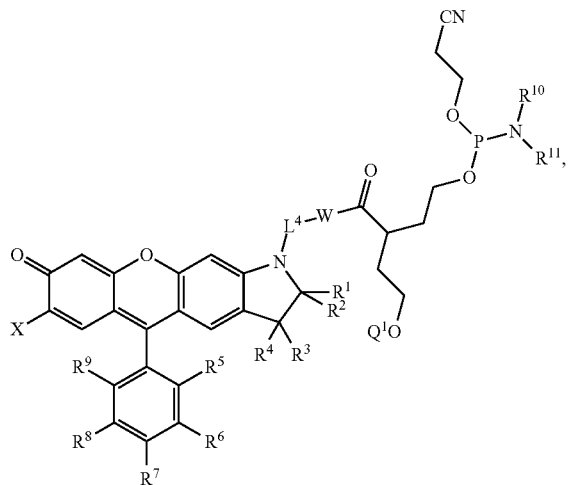

(ID)

or a stereoisomer, a salt, or a tautomer thereof, wherein W is NH or O, and $L^4$ is an optionally substituted $C_2$-$C_{10}$ alkylene or optionally substituted $C_2$-$C_{50}$ heteroalkylene.

In the Formulae shown herein, $Q^1$ denotes a hydroxyl protecting group. Examples of such protective groups are known in the art (See, e.g., Peter G. M. Wuts, Greene's protective groups in organic synthesis (2006)). Suitable hydroxyl protecting groups include base-labile and acid-labile groups. In some embodiments, Q is a hydroxyl protective group that is compatible with the automated phosphoramidite oligonucleotide synthesis conditions, such as a trityl or dimethoxytrityl group. In some embodiments, $Q^1$ is trimethylsilyl, TBDMS, acetyl, dimethoxy trityl, or trityl.

In some embodiments, $R^5$ is methyl or halogen such as Cl or F. In some embodiments, $R^7$ is methyl or halogen such as Cl or F. In some embodiments, $R^8$ is methyl or halogen such as Cl or F. In some embodiments, $R^7$ is H. In some embodiments, $R^6$ and $R^9$ are H.

In some embodiments, the compound is a compound of formula (IE):

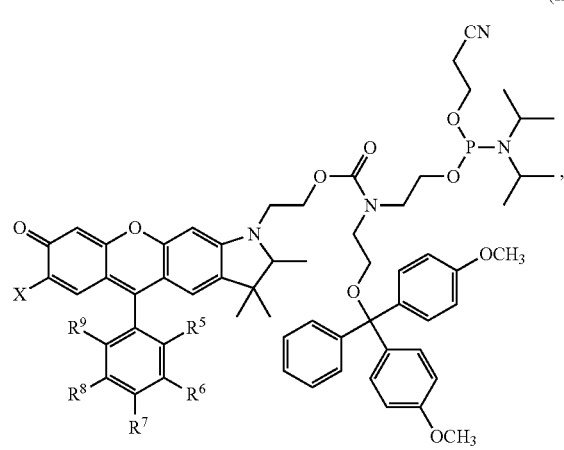

(IE)

or a stereoisomer, a salt, or a tautomer thereof.

In some embodiments of Formula (I), Y is a solid support such as a controlled pore glass or polystyrene. In some embodiments of Formula (I), Y optionally comprises a linking group linking the controlled pore glass or polystyrene with the rest of the structure.

In another aspect, the disclosure provides a compound of Formula II:

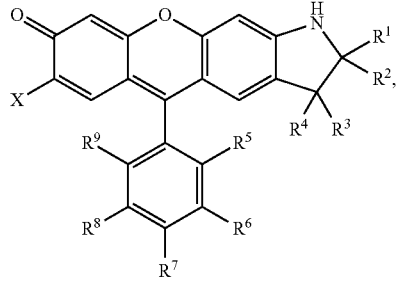

or a stereoisomer, a salt, or a tautomer thereof.

wherein X is H, halogen, or an optionally substituted $C_1$-$C_5$ alkyl;

$R^1$, $R^2$, $R^3$, and $R^4$ are independently H or optionally substituted $C_1$-$C_6$ alkyl; and $R^5$, $R^6$, $R^7$, $R^8$, and $R^9$ are independently H, halogen, or optionally substituted $C_1$-$C_6$ alkyl.

In some embodiments of Formula II, X is Cl, Br, or F. In some embodiments, X is Cl. In some embodiments, X is F.

In some embodiments of Formula II, $R^1$ is H. In some embodiments, $R^2$ is methyl. In some embodiments, $R^3$ is methyl. In some embodiments, $R^4$ is methyl. In some embodiments, $R^1$ is H, and each of $R^2$, $R^3$, and $R^4$ is methyl.

As used herein, the terms "alkyl," "alkenyl," and "alkynyl" include straight-chain, branched-chain, and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C, as $C_1$-$C_{10}$, C—C10, or C1-10.

The terms "heteroalkyl," "heteroalkenyl," and "heteroalkynyl," as used herein, mean the corresponding hydrocarbons wherein one or more chain carbon atoms have been replaced by a heteroatom. Exemplary heteroatoms include N, O, S, and P. When heteroatoms are allowed to replace carbon atoms, for example, in heteroalkyl groups, the numbers describing the group, though still written as e.g. C3-C10, represent the sum of the number of carbon atoms in the cycle or chain and the number of such heteroatoms that are included as replacements for carbon atoms in the cycle or chain being described.

Typically, the alkyl, alkenyl, and alkynyl substituents contain 1-10 carbon atoms (alkyl) or 2-10 carbon atoms (alkenyl or alkynyl). Preferably, they contain 1-8 carbon atoms (alkyl) or 2-8 carbon atoms (alkenyl or alkynyl). Sometimes they contain 1-6 carbon atoms (alkyl) or 2-6 carbon atoms (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

As used herein, the terms "alkylene," "alkenylene," and "alkynylene" include straight-chain, branched-chain, and cyclic divalent hydrocarbyl radicals, and combinations thereof.

Alkyl, alkenyl, and alkynyl groups can be optionally substituted to the extent that such substitution makes sense chemically. Typical substituents include, but are not limited to, halogens (F, Cl, Br, I), =O, =N—CN, =N—OR, =NR, OR, $NR_2$, SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, and $NO_2$, wherein each R is independently H, $C_1$-$C_8$ alkyl, $C_2$-$C_8$ heteroalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each R is optionally substituted with halogens (F, Cl, Br, I), =O, =N—CN, =N—OR', =NR, OR', $NR'_2$, SR, $SO_2R'$, $SO_2NR'_2$, $NR'SO_2R'$, $NR'CONR'_2$, NR'C(O)OR', NR'C(O)R', CN, C(O)OR', C(O)$NR'_2$, OC(O)R', C(O)R', and $NO_2$, wherein each R is independently H, $C_1$-$C_8$ alkyl, $C_2$-$C_8$ heteroalkyl, $C_1$-$C_8$ acyl, $C_2$-$C_8$ heteroacyl, $C_6$-$C_{10}$ aryl, or $C_5$-$C_{10}$ heteroaryl. Alkyl, alkenyl and alkynyl groups can also be substituted by $C_1$-$C_8$ acyl, $C_2$-$C_8$ heteroacyl, $C_6$-$C_{10}$ aryl, or $C_5$-$C_{10}$ heteroaryl, each of which can be substituted by the substituents that are appropriate for the particular group.

While "alkyl" as used herein includes cycloalkyl and cycloalkylalkyl groups, the term "cycloalkyl" is used herein to describe a carbocyclic non-aromatic group that is connected via a ring carbon atom, and "cycloalkylalkyl" is used to describe a carbocyclic non-aromatic group that is connected to the molecule through an alkyl linker. Similarly, "heterocyclyl" is used to identify a non-aromatic cyclic group that contains at least one heteroatom as a ring member and that is connected to the molecule via a ring atom, which may be C or N; and "heterocyclylalkyl" may be used to describe such a group that is connected to another molecule through an alkylene linker. As used herein, these terms also include rings that contain a double bond or two, as long as the ring is not aromatic.

"Aromatic" or "aryl" substituent or moiety refers to a monocyclic or fused bicyclic moiety having the well-known characteristics of aromaticity; examples include phenyl and naphthyl. Similarly, the terms "heteroaromatic" and "heteroaryl" refer to such monocyclic or fused bicyclic ring systems which contain as ring members one or more heteroatoms. Suitable heteroatoms include N, O, and S, inclusion of which permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl, and fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably, the monocyclic heteroaryls contain 5-6 ring members, and the bicyclic heteroaryls contain 8-10 ring members.

Aryl and heteroaryl moieties can be substituted with a variety of substituents including $C_1$-$C_8$ alkyl, $C_2$-$C_8$ alkenyl, $C_2$-$C_8$ alkynyl, $C_5$-$C_{12}$ aryl, $C_1$-$C_8$ acyl, and heteroforms of these, each of which can itself be further substituted; other substituents for aryl and heteroaryl moieties include halogens (F, Cl, Br, I), OR, $NR_2$, SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, and $NO_2$, wherein each R is independently H, $C_1$-$C_8$ alkyl, $C_2$-$C_8$ heteroalkyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, $C_5$-$C_{10}$ heteroaryl, $C_7$-$C_{12}$ arylalkyl, or $C_6$-$C_{12}$ heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

"Optionally substituted," as used herein, indicates that the particular group being described may have one or more hydrogen substituents replaced by a non-hydrogen substituent. In some optionally substituted groups or moieties, all hydrogen substituents are replaced by a non-hydrogen substituent, e.g., $C_1$-$C_6$ alkyl, $C_2$-$C_6$ heteroalkyl, alkynyl, halogens (F, Cl, Br, $N_3$, OR, $NR_2$, SR, $SO_2R$, $SO_2NR_2$, $NRSO_2R$, $NRCONR_2$, NRC(O)OR, NRC(O)R, CN, C(O)OR, C(O)$NR_2$, OC(O)R, C(O)R, oxo, and $NO_2$, wherein each R is independently H, $C_1$-$C_6$ alkyl, or $C_2$-$C_6$ heteroalkyl. Where an optional substituent is attached via a double bond, such as a carbonyl oxygen or oxo (=O), the group takes up two available valences, so the total number of substituents that may be included is reduced according to the number of available valences.

Salts, stereoisomers, and tautomers of the compounds disclosed herein are also within the scope of this disclosure. As used herein, "stereoisomer" or "stereoisomers" refer to compounds that differ in the chirality of one or more stereocenters. Stereoisomers include enantiomers and diastereomers. As used herein, "tautomer" refers to alternate forms of a compound that differ in the position of a proton, such as enol-keto and imine-enamine tautomers. As used herein, "salt" of a compound refers to an ion of the compound ionically association with a counterion. A salt of a compound can be formed by the neutralization reaction of an acid and a base. Salts can be derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate. Although structures of the compounds disclosed herein can be shown in only one resonance form, it is understood that all resonance forms are included.

The dyes of the disclosure can be prepared by any suitable method. For example, dyes can be prepared according to the methods shown in the Reaction Schemes I and II below.

In another aspect, provided herein are fluorescent dye-labeled polynucleotides prepared by an automated oligonucleotide synthesis using the fluorescent dye phosphoramidites disclosed herein. The polynucleotides comprise a moiety derived from a compound of the disclosure. As used herein, "fluorescent dye-labeled polynucleotide" or "labeled polynucleotide" refers to a polynucleotide that prepared by an automated oligonucleotide synthesis from compounds of the Formulae disclosed herein.

Labeled polynucleotides disclosed herein can comprise one or more additional moieties. In some embodiments of the present disclosure, a labeled polynucleotide comprises a minor groove binder. In some embodiments, a labeled polynucleotide comprises an intercalator. In some embodiments, a labeled polynucleotide comprises a second fluorophore and/or a fluorescence quencher.

Typically, a polynucleotide labeled with the dyes disclosed herein is a polynucleotide wherein the backbone comprises 2'-deoxyribose or ribose. However, a labeled polynucleotide can comprise one or more modifications. In some embodiments, a polynucleotide comprises a sugar modification, e.g., a modified sugar. Various sugar modifications are useful. Some non-limiting sugar modifications include arabinose, d-arabino-hexitol, 2-fluoroarabinose, xylulose, hexose, or a bicyclic sugar.

A labeled polynucleotide of the disclosure can comprise one or more backbone modifications. In some embodiments, the polynucleotide comprises a backbone modification. In some embodiments, a backbone modification is selected from the group consisting of a modified sugar phosphate backbone, a locked nucleic acid backbone, a peptidic backbone, a phosphotriester backbone, a phosphoramidate backbone, a siloxane backbone, a carboxymethylester backbone, an acetamidate backbone, a carbamate backbone, a thioether backbone, a bridged methylene phosphonate backbone, a phosphorothioate backbone, a methylphosphonate backbone, an alkylphosphonate backbone, a phosphate ester backbone, an alkylphosphonothioate backbone, a phosphorodithioate backbone, a carbonate backbone, a phosphate triester backbone, a carboxymethyl ester backbone, a methylphosphorothioate backbone, a phosphorodithioate backbone, a backbone having p-ethoxy linkages, and a combination of two or more of any of the foregoing. In a particular embodiment of the present disclosure, the backbone modification is a modified sugar phosphate backbone.

Labeled polynucleotides disclosed herein can comprise one or more modified or unnatural bases. Modified bases include modified thymine and cytosine bases (e.g, those disclosed in U.S. Pat. Nos. 9,598,455 and 9,598,456), 2,6-diaminopurine bases, universal bases, and the like. Labeled polynucleotides disclosed herein can comprise non-nucleoside segments or non-nucleoside monomers (e.g., linkers such as poly(ethyleneglycol) linkers).

In some embodiments, the polynucleotide disclosed herein is probe, e.g. a 5'-nuclease PCR probe. In certain embodiments, the polynucleotide further comprises one or more additional labels, for example, a fluorescence quencher. As one of ordinary skill in the art will appreciate, the location of a label within the oligonucleotide can vary and is not limited to the disclosure herein.

In some embodiments, provided herein is a modified polynucleotide which comprises a dye moiety as a fluorophore on one end of its sequence and a fluorescence quencher on the other end of its sequence, so that the fluorescence quencher suppresses the fluorescence signal of the fluorophore in the intact probe (i.e., the oligonucleotide being used as a probe) via an energy transfer mechanism such as fluorescence resonance energy transfer ("FRET"). When a polymerase extends a primer along a template to which the probe has also hybridized, the 5'-nuclease activity of the polymerase cleaves the probe, thereby allowing the fluorophore to diffuse away from the fluorescence quencher so that the fluorescent signal is now detected. The signal increases with each PCR cycle proportionally to the amount of probe that is cleaved, and thus, proportionally to the amount of amplification product (e.g., amplicon, target sequence). This allows direct detection and quantification of the target DNA sequence.

In some embodiments, the dye moiety is at least one nucleotide position away from the end of the sequence of the labeled polynucleotide and the fluorescence quencher is attached to a base that is at least one nucleotide position away from the other end of the modified polynucleotide. In some embodiments, the dye moiety and the fluorescence quencher are located internally within a probe. As one of ordinary skill in the art will appreciate, the location of the fluorophore and/or the fluorescence quencher within a probe can vary and is not limited.

In some embodiments, the dye moiety and fluorescence quencher are not at the ends of a FRET probe. In some embodiments, the emission spectrum of the dye overlaps considerably with the absorption spectrum of the fluorescence quencher. However, such spectral overlap is less important or not required when quenching involves a collisional mechanism, or the overlap is increased, for example, due to reaction conditions or probe structure.

A great deal of practical guidance available in the art for selecting appropriate fluorophore-quencher pairs for particular probes. See, for example, FLUORESCENCE SPECTROSCOPY (Marcel Dekker, New York, 1971). Quenchers useful for inclusion in probes disclosed herein include bis-azoquenchers (e.g., those disclosed in U.S. Pat. No. 6,790,945), quenchers available from Biosearch Technologies, Inc. (Black Hole™ Quenchers: BHQ-1, BHQ-2, and BHQ-3), TAMRA, carboxytetramethyl rhodamine, 4-((4-(dimethylamino)phenyl)azo)benzoic acid (Dabcyl), Zen® quencher, Blackberry® quencher, 2,3-Dichloro-5,6-dicyano-1,4-benzoquinone (DDQ)-I, and 2-[6-(1,3-dihydro-2H-isoindol-2-yl)-9-{2-[(4-[(2,5-dioxopyrrolidin-1-yl)o-xy] carbonyl piperidin-1-yl) sulfonyl]phenyl}-3H-xanthen-3-ylidene]-2,3-dihydro-1H-isoindolium chloride (QSY 21) and other known in the art quenchers.

In yet another aspect, disclosed herein is a method for preparing a labeled conjugate of a ligand, comprising contacting a ligand with a compound of a Formulae provided herein in a suitable solvent under conditions sufficient to covalently attach the compound to the ligand thereby forming the dye-labeled conjugate. Suitable ligands include biomolecules (e.g., a polynucleotide, an oligonucleotide, a protein, an antibody, a peptide, or a polysaccharide), synthetic polymers (e.g., a polymer with an ethylenic backbone, such as polyacrylic acid), and solid supports (e.g., controlled pore glass or polystyrene).

In some embodiments, the ligand is a polynucleotide. In some embodiments, the conditions sufficient to covalently attach the compound of the present disclosure to the ligand, i.e., oligonucleotide or polynucleotide, are automated phosphoramidite oligonucleotide synthesis conditions. Automated phosphoramidite oligonucleotide synthesis conditions used to synthesize and deprotect synthetic oligonucleotides are well-known in the art, and are described, for example, in Current Protocols in Nucleic Acid Chemistry, Vol. I, Beaucage et al., Eds., John Wiley & Sons, 2002, the disclosure of which are incorporated herein by reference.

The phosphoramidite method of oligonucleotide, e.g., DNA, synthesis is considered as the standard synthesis method used in most automated synthesizers. Building blocks used for synthesis are commonly referred to as nucleotide building blocks, monomers, or nucleoside phosphoramidites, which are activated nucleoside derivatives (phosphoramidites). An acid-cleavable protecting group, typically, the dimethoxytrityl (DMT) group, is used to protect the 5'-end of the nucleoside and a O-cyanoethyl group is used to protect the 3'-phosphite moiety. A monomer may also include additional groups that serve to protect other moieties, e.g., reactive primary amines in the nucleobases. The protecting groups are selected to prevent branching or other undesirable side reactions from occurring during synthesis. Skilled artisans will be readily able to select protecting groups having properties suitable for use under specific synthesis and deprotection and/or cleavage conditions. A wide variety of amine protecting groups are taught, for example in, Greene & Wuts, "Protective Groups In Organic Chemistry," 3d Edition, John Wiley & Sons, 1999 (hereinafter "Green & Wuts").

Typically, oligonucleotides are synthesized on solid supports, e.g., control pore glass (CPG)- or polystyrene-filled column, a membrane, or a similar material. An oligonucleotide is usually synthesized from the 3' to the 5'-end. The first nucleotide building block or monomer is usually anchored to the support, typically, via a linker, such as a long chain alkylamine-controlled pore glass (LCAA-CPG).

In some embodiments, synthesis methods that employ phosphoramidite reagents involve multiple rounds of: (i) DMT deprotection to reveal a free hydroxyl, which can be effected, for example, by treatment with 2.5% or 3% di- or tri-chloroacetic acid in dichloromethane; (ii) coupling of nucleoside or other phosphoramidite reagents to the free hydroxyl, which can be carried out, for example, in acetonitrile containing tetrazole (e.g., 0.45 M or 0.5 M tetrazole); (iii) oxidation, which can be carried out, for example, by treatment with $I_2$/2,6-lutidine/$H_2O$; and capping, which can be carried out, for example, by treatment with 6.5% acetic anhydride in tetrahydrofuran (THF) activated with 10% 1-methylimidazole (NMI) in THF.

Other conditions for carrying out the various steps in the synthesis are also known in the art and can be used herein. For example, phosphoramidite coupling can be carried out in acetonitrile containing 0.25 M 5-ethylthio-1H-tetrazole, 0.25 M 4,5-dicyanoimidazole (DCI) or 0.25 M 5-benzylthio-1H-tetrazole (BTT). Oxidation can be carried out with 0.1 M, 0.05 M or 0.02 M $I_2$ in THF/$H_2O$/pyridine (7:2:1). Capping can be carried out by treatment with THF/lutidine/acetic anhydride followed by treatment with 16% NMI in THF.

Removal of any protecting groups and cleavage from the synthesis reagent is typically achieved by treatment with concentrated ammonium hydroxide at 60° C. for 1-12 hours, although nucleoside phosphoramidites protected with groups that can be removed under milder conditions, such as by treatment with concentrated ammonium hydroxide at room temperature for 4-17 hours or treatment with 0.05 M potassium carbonate in methanol, or treatment with 25% t-butylamine in water/EtOH, are also known and can be used.

The term "cleavage" in reference to solid phase oligonucleotide synthesis means breaking the bond which attaches an oligonucleotide to a solid phase support. In some embodiments, cleavage involves hydrolysis of a succinate ester bond between the 3' hydroxyl of an attached oligonucleotide and the solid phase support.

The term "deprotection" as used herein means removing protection groups from the exocyclic amines of the heterocyclic bases of an oligonucleotide. Usually, deprotection involves hydrolysis of an amide moiety consisting of an exocyclic amine and an amino protection group, e.g. benzoyl or isobutyryl. Various techniques and methods of deprotection are known in the art.

In another aspect, provided herein are kits comprising the labeled polynucleotides or the compounds of the disclosure. In some embodiments, the kit is a PCR diagnostic kit comprising one or more polynucleotides of the disclosure. In some embodiments, the kit is an automated molecular diagnostics cartridge.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

The invention is illustrated by the following Examples. These Examples are included for illustrative purposes only and are not intended to limit the invention.

Examples

Proton ($^1$H, 400 MHz) and phosphorous ($^{31}$P, 160 MHz) nuclear magnetic resonance (NMR) spectra are obtained on a Bruker Biospin 400 instrument. NMR samples are prepared in DMSO-$d_6$ and $CD_3CN$ and residual protonated solvent is used as an internal chemical shift standard. LCMS data are obtained by electrospray ionization (ESI) on Agilent 1200 series (LC/MSD Trap XCT Plus) and Agilent 1260 infinity (6130 Quadrupole LC/MS) instruments. Automated chromatography on silica gel 60 is carried out using Biotage Isolera LS and Teledyne ISCO Torrent® Combi Flash instruments. Analytical thin layer chromatography is conducted on aluminum-backed silica gel 60 F254, and plates are visualized under a UV lamp (254 and 365 nm). All reagents are from commercial sources unless indicated otherwise.

Polynucleotides comprising the compounds of the disclosure are synthesized on a MerMade-12 oligonucleotide synthesizer utilizing standard 200 nmol DNA protocol in cycles of DMT removal-coupling-capping-oxidation-capping. Coupling time for dye phosphoramidites of the disclosure can be adjusted accordingly.

For polynucleotides containing 5' dyes, synthesis is completed after the last dye phosphoramidite coupling cycle. In case of internal incorporation of the dye phosphoramidites, more nucleoside monomers are added after the coupling of the dye. A final DMT group is left on polynucleotide.

Fully assembled polynucleotides are cleaved from solid support and deprotected by 30% ammonium hydroxide at 55° C. for 10-12 h. After the removal of ammonia, oligonucleotides are analyzed and purified by reverse-phase HPLC (RP-HPLC) on C18 Gemini column eluting with a linear gradient of acetonitrile/0.1 M triethylammonium bicarbonate, pH 7. After DMT group removal, polynucleotides are purified for the second time. Excitation and emission spectra of labeled oligonucleotides are recorded on an Agilent Cary fluorimeter (200 nM oligonucleotide, 0.1 M Tris buffer, pH 8).

An exemplary method of synthesis of exemplary fluorescent dye phosphoramidites of the disclosure (e.g., compound D), is shown in the reaction scheme I.

First, the starting alcohol compound A (e.g., a compound of Table I) is acylated with bis(4-nitrophenyl) carbonate in the presence of base in situ followed by nucleophilic substitution of 4-nitrophenyl ester with a secondary amine with formation of carbamate bond to yield the intermediate product C. The product can be isolated by flash chromatography. Compound C is transformed into phosphoramidite D using standard phosphitylation under anhydrous conditions with exclusion of acids. The reaction mixture and the product are protected from light and air (oxygen). The product is purified using flash chromatography on silica gel.

Reaction Scheme I
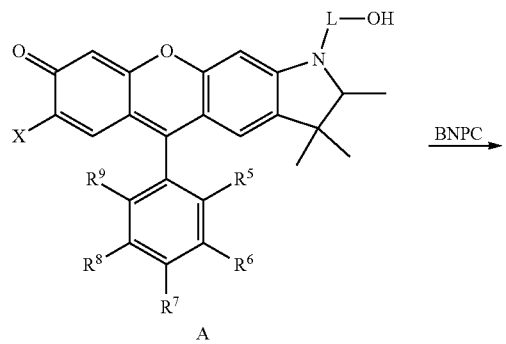
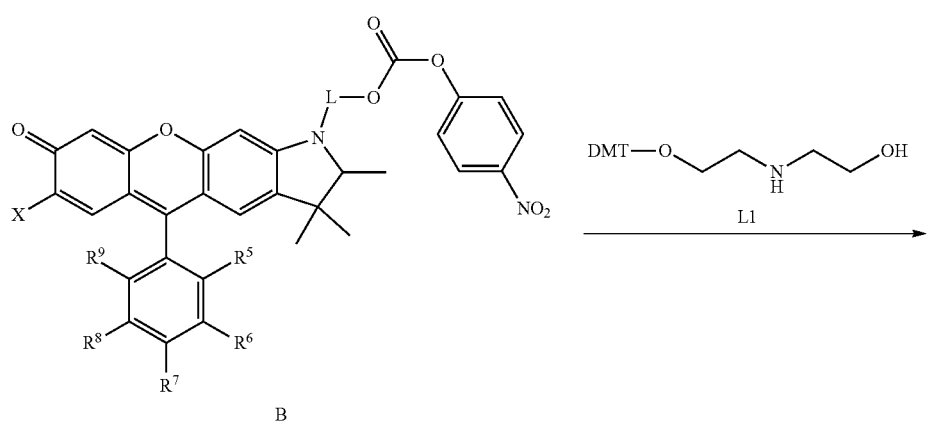
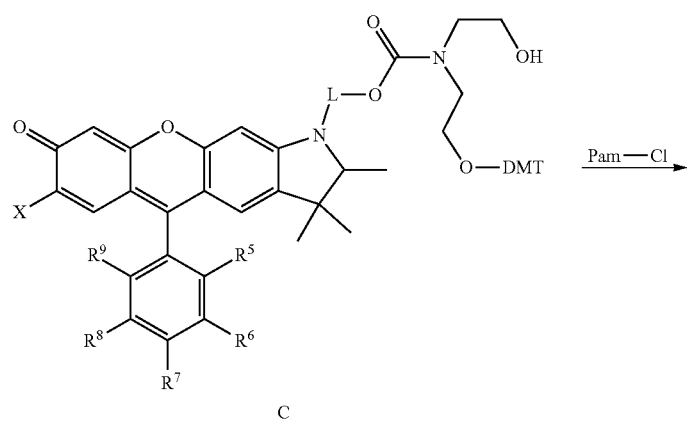

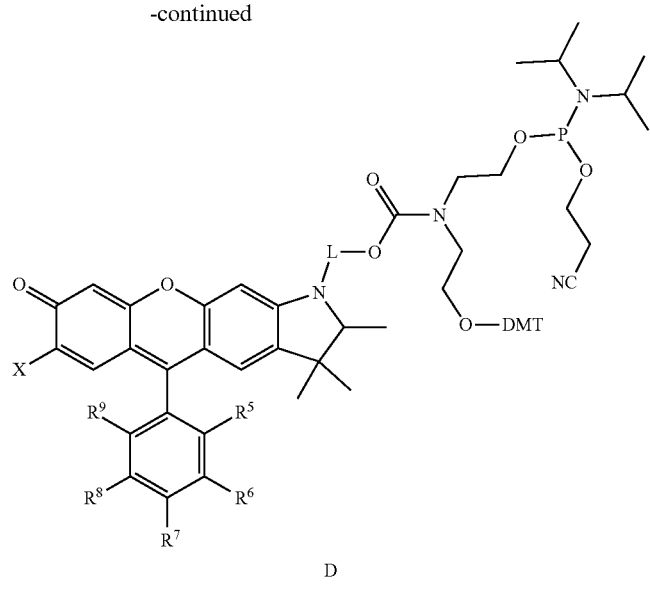
D
Alcohol compounds A, such as compounds of Table 1, can be prepared according to the method shown in the reaction scheme II.
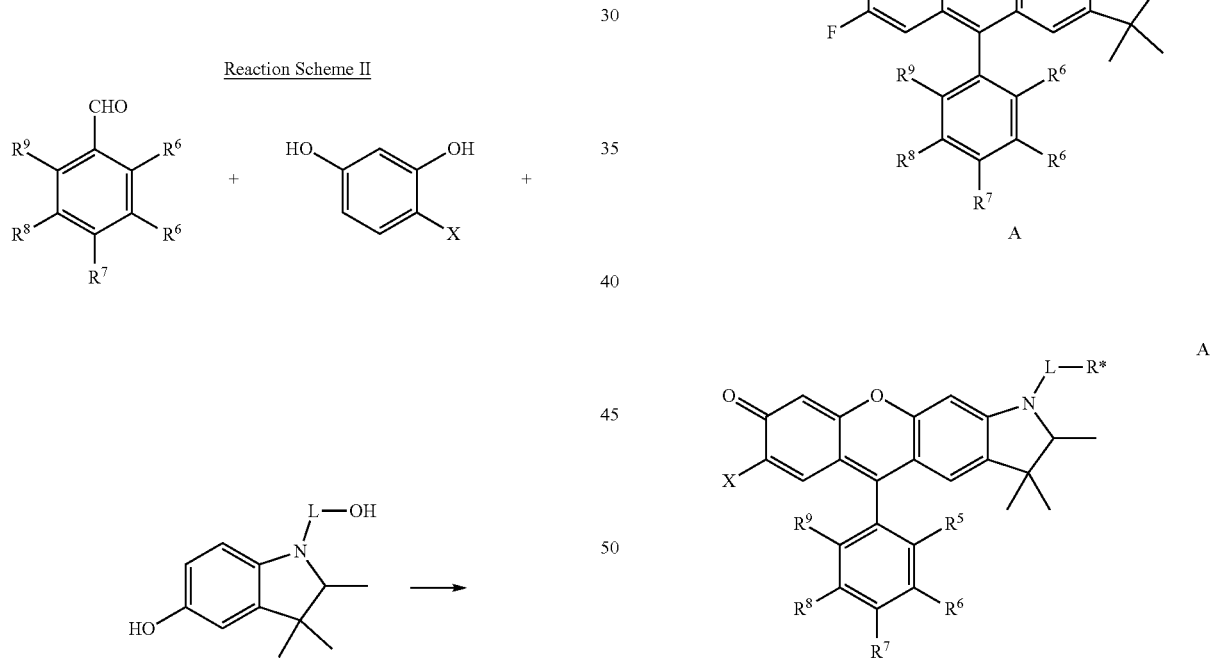
A
TABLE 1
| A | X | R⁵ | R⁶ | R⁷ | R⁸ | R⁹ | L-R* | λ$_{max}$ (HPLC) | λ$_{ex}$ | λ$_{em}$ |
|---|---|---|---|---|---|---|---|---|---|---|
| 1 | H | Me | H | H | H | H | CH₂CH₂OH | — | 522 | 543 |
| 2 | o-MeC₆H₄CH₂ | Me | H | H | H | H | CH₂CH₂OH | 539 | 526 | 548 |
| 3 | H | Cl | H | H | H | H | CH₂C(O)NHCH₂CH₂OCH₂CH₂OH | 530 | 525 | 546 |
| 4 | H | Cl | H | H | H | H | CH₂C(O)N(Me)CH₂CH₂OH | — | 528 | 547 |
| 5 | H | Cl | H | H | H | H | CH₂CH₂OH | 537 | 530 | 551 |
| 6 | H | Cl | H | H | H | H | CH₂CH₂CH₂OH | 538 | 531 | 552 |

TABLE 1-continued

| A | X | $R^5$ | $R^6$ | $R^7$ | $R^8$ | $R^9$ | L-R* | $\lambda_{max}$ (HPLC) | $\lambda_{ex}$ | $\lambda_{em}$ |
|---|---|---|---|---|---|---|---|---|---|---|
| 7 | Et | Cl | H | H | H | H | CH$_2$CH$_2$OH | — | 557 | 578 |
| 8 | H | F | H | H | F | H | CH$_2$CH$_2$OH | — | 536 | 558 |
| 9 | Cl | Me | H | H | H | H | CH$_2$CH$_2$OC(O)Et | — | 528 | 546 |
| 10 | Cl | Me | H | H | H | H | CH$_2$CH$_2$OH | 536 | 529 | 548 |
| 11 | Cl | Et | H | H | H | H | CH$_2$CH$_2$OH | — | 529 | 548 |
| 12 | Cl | Me | H | H | Me | H | CH$_2$CH$_2$OH | 535 | 528 | 547 |
| 13 | Cl | Me | H | Me | Me | H | CH$_2$CH$_2$OH | 534 | 528 | 547 |
| 14 | F | Me | H | H | Me | H | CH$_2$CH$_2$OH | 527 | 521 | 544 |
| 15 | F | Me | H | H | H | H | CH$_2$CH$_2$OH | 528 | 523 | 545 |
| 16 | F | Me | H | H | H | H | (CH$_2$)$_6$OH | 529 | 524 | 546 |
| 17 | F | Me | H | H | F | H | CH$_2$CH$_2$OH | 530 | 525 | 546 |
| 18 | F | Me | H | F | H | H | CH$_2$CH$_2$OH | 530 | 525 | 546 |
| 19 | F | Me | H | Me | Me | H | CH$_2$CH$_2$OH | — | 528 | 546 |

Preparation of Precursor Alcohol a (Compound 19A).

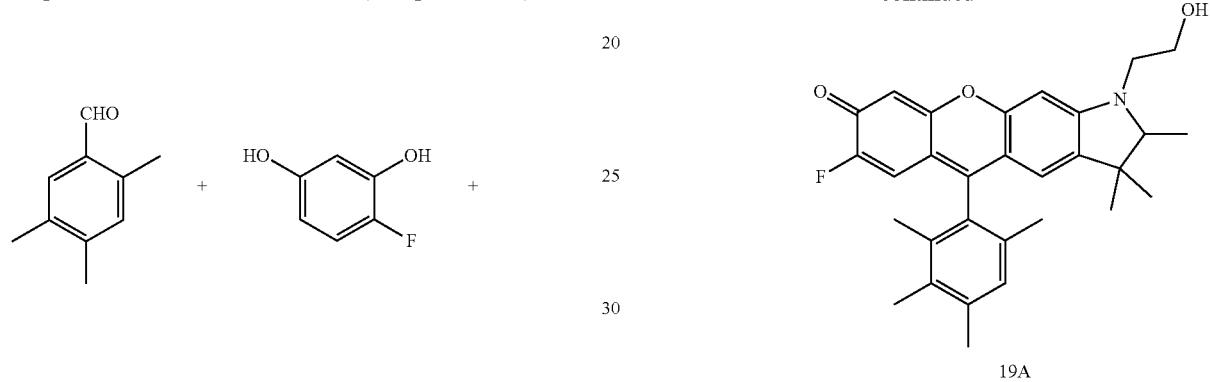

Under a dry, inert atmosphere, 2,3-dihydro-2,3,3-trimethyl-1-(2-hydroxyethyl)-indol-5-ol (prepared according to the procedure of WO 2019/217470; 28.0 mmol) and 4-fluororesorcinol (56.0 mmol) were suspended in 50 mL of methanesulfonic acid. The solution was heated at 55° C. until it became homogenous. To the solution, 2,4,5-trimethylbenzaldehyde (61.6 mmol) in methanesulfonic acid (15 mL) was added, and the mixture was heated at 55° C. for 1.5 h. The reaction flask was placed in an ice bath, and 150 g of crushed ice with 125 ml of water were added. The mixture was extracted with THF/CHCl$_3$ (1:2) three times, and the combined organic layers were extracted with saturated NaHCO$_3$ and dried over anhydrous Na$_2$SO$_4$. Silica gel chromatography with acetonitrile/water provided 3.67 mmol (13%) of the dye Compound 19 A with the excitation/emission maxima of 528 nm/546 nm, respectively.

Preparation of Exemplary Phosphoramidite (Compound 19D).

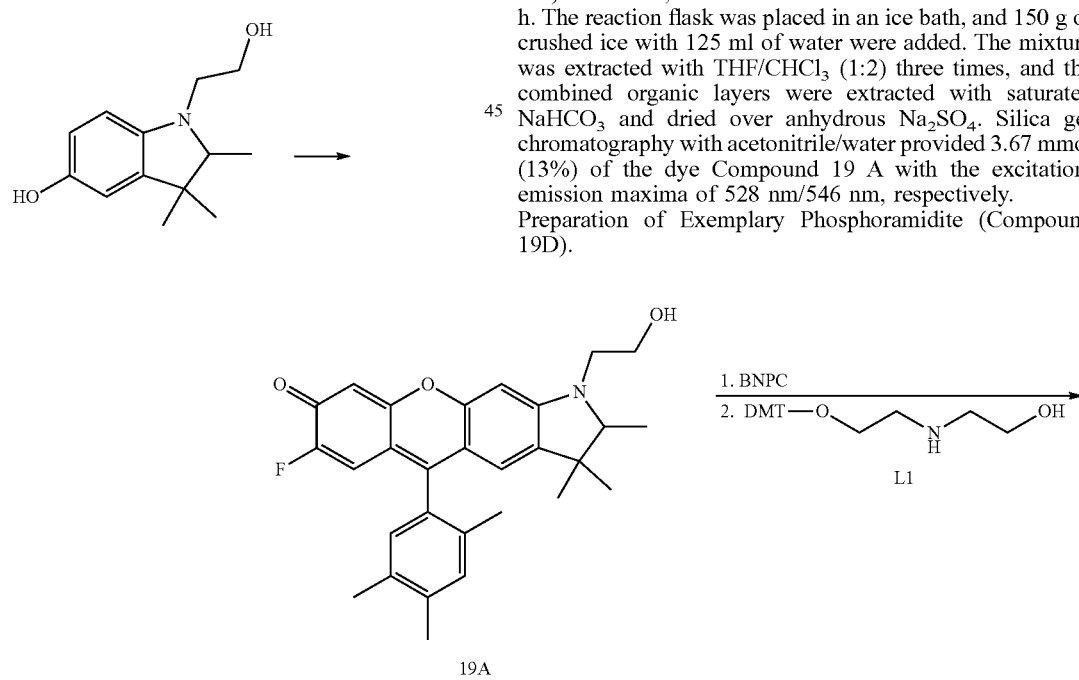

-continued

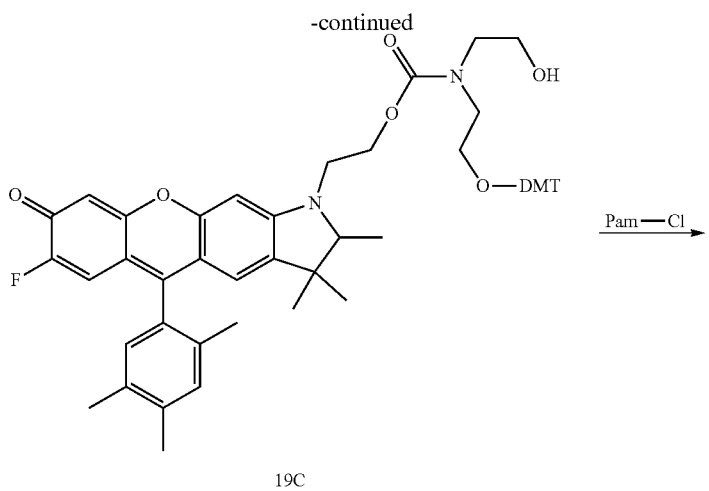

19C

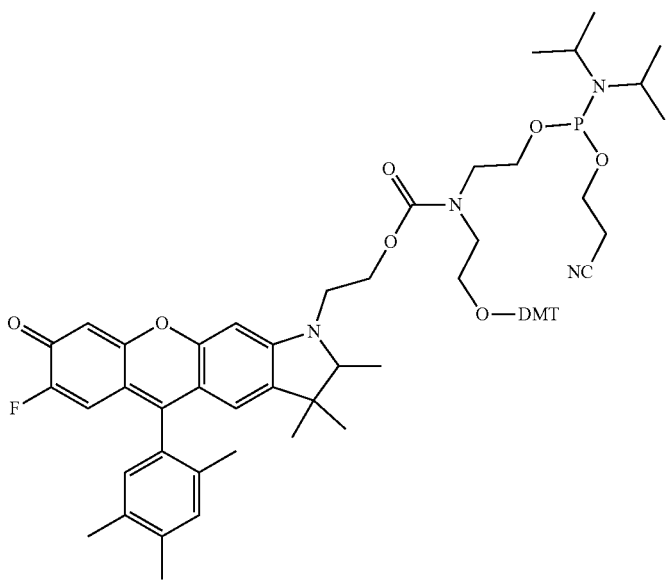

19D

To a solution of Compound 19A in anhydrous N,N-dimethylformamide, triethylamine is added followed by BNPC in one portion under argon atmosphere. The reaction is incubated for 40 min Linker compound L1 is added into the reaction mixture, and the reaction mixture is incubated at ambient temperature for 2.5 h. The reaction mixture is transferred into a separatory funnel rinsing the reaction flask with ethyl acetate. The solution is extracted with water. The aqueous layer is discarded, and the organic layer is further washed with DI water and saturated aqueous sodium chloride and is dried over anhydrous sodium sulfate with stirring for 18 h. The crude product is purified by flash chromatography to yield Compound 19C.

Compound 19C is dissolved in anhydrous dichloromethane under argon, and anhydrous N,N-diisopropylethylamine is charged via syringe with stirring. The reaction flask is placed in ice bath for 10 min to cool the reaction mixture to <10° C. Pam-Cl is added dropwise via syringe during 1 min, and the reaction mixture is removed from ice. The reaction mixture is protected from light by wrapping the flask with aluminum foil and is allowed to gradually warm to room temperature for 2.5 h. The reaction mixture is diluted with ethyl acetate and transferred into a separatory funnel under argon. Following the transfer, the reaction mixture is extracted with 10% saturated sodium bicarbonate solution Aqueous layer is discarded and the organic layer is extracted with saturated sodium chloride to remove water. The organic layer is dried over anhydrous sodium sulfate under argon protected from light. After drying, the solution is filtered, and the solvents are evaporated to yield the crude product as red foam. The crude product is purified by flash chromatography. The product Compound 19D is analyzed by HPLC. LC-MS, and NMR.

While illustrative embodiments have been illustrated and described, it will be appreciated that various changes can be made therein without departing from the spirit and scope of the invention.

We claim:

1. A compound represented by Formula I:

(I)

[Chemical structure of Formula I]

or a stereoisomer, a salt, or a tautomer thereof,
wherein:
X is H, halogen, or $C_1$-$C_5$ alkyl;
$R^1$, $R^2$, $R^3$, and $R^4$ are independently H or optionally substituted $C_1$-$C_6$ alkyl;
$R^5$, $R^6$, $R^7$, $R^8$, and $R^9$ are independently H, halogen, or optionally substituted $C_1$-$C_6$ alkyl;
$L^1$ is an optionally substituted $C_2$-$C_{10}$ alkylene or optionally substituted $C_2$-$C_{50}$ heteroalkylene;
$L^2$ and $L^3$ are independently an optionally substituted $C_2$-$C_{10}$ alkylene or optionally substituted $C_2$-$C_{30}$ heteroalkylene;
$Q^1$ is a hydroxyl protecting group;
Z is CH, N, NHC(O)N, or OC(O)N;
Y is OH, OP(OCH$_2$CH$_2$CN)NR$^{10}$R$^{11}$ or a solid support; and
$R^{10}$ and $R^{11}$ are independently optionally substituted $C_1$-$C_6$ alkyl,
wherein optionally substituted alkyl refers to alkyl optionally substituted with F, Cl, Br, I, =O, =N—CN, =N—OR, =NR, OR, NR$_2$, SR, SO$_2$R, SO$_2$NR$_2$, NRSO$_2$R, NRCONR$_2$, NRC(O)OR, NRC(O)R, CN, C(O)OR, C(O)NR$_2$, OC(O)R, C(O)R, or NO$_2$, wherein each R is independently H, $C_1$-$C_8$ alkyl, $C_2$-$C_8$ heteroalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each R is optionally substituted with F, Cl, Br, I, =O, =N—CN, =N—OW, =NR', OR', NR'$_2$, SR', SO$_2$R', SO$_2$NR'$_2$, NR'SO$_2$R', NR'CONR'$_2$, NR'C(O)OR', NR'C(O)R', CN, C(O)OR', C(O)NR'$_2$, OC(O)R', C(O)R', and NO$_2$, wherein each R' is independently H, $C_1$-$C_8$ alkyl, $C_2$-$C_8$ heteroalkyl, $C_1$-$C_8$ acyl, $C_2$-$C_8$ heteroacyl, $C_6$-$C_{10}$ aryl, or $C_5$-$C_{10}$ heteroaryl,
wherein optionally substituted heteroalkylene refers to heteroalkylene optionally substituted with $C_1$-$C_6$ alkyl, $C_2$-$C_6$ heteroalkyl, alkynyl, F, Cl, Br, I, N$_3$, OR, NR$_2$, SR, SO$_2$R, SO$_2$NR$_2$, NRSO$_2$R, NRCONR$_2$, NRC(O)OR, NRC(O)R, CN, C(O)OR, C(O)NR$_2$, OC(O)R, C(O)R, oxo, and NO$_2$, wherein each R is independently H, $C_1$-$C_6$ alkyl, or $C_2$-$C_6$ heteroalkyl,
wherein heteroalkylene, heteroalkyl, heteroalkenyl, heteroalkynyl, and heteroacyl, refer to the corresponding hydrocarbon wherein one or more chain carbon atoms have been replaced by a heteroatom selected from the group consisting of N, O, S, and P, and wherein heteroaryl refers to a monocyclic or fused bicyclic aromatic ring system which contains as ring members one or more heteroatoms selected from the group consisting of N, O, and S.

2. The compound of claim 1, wherein X is Cl, Br, or F.

3. The compound of claim 1, wherein X is Cl.

4. The compound of claim 1, wherein the solid support is controlled pore glass or polystyrene.

5. The compound of claim 1, wherein the compound is compound of formula (IA):

(IA)

[Chemical structure of Formula IA]

or a stereoisomer, a salt, or a tautomer thereof.

6. The compound of claim 1, wherein $R^1$ is H.

7. The compound of claim 1, wherein $R^2$ is methyl.

8. The compound of claim 1, wherein $R^3$ is methyl.

9. The compound of claim 1, wherein $R^4$ is methyl.

10. The compound of claim 1, wherein the compound is a compound of formula (IB):

(IB)

[Chemical structure of Formula IB]

or a stereoisomer, a salt, or a tautomer thereof.

11. The compound of claim 1, wherein $L^1$ is $C_2$-$C_6$ alkylene or —(CH$_2$CH$_2$O)$_m$CH$_2$CH$_2$—, wherein m is an integer from 1 to 10.

12. The compound of claim 1, wherein $L^1$ is $C_2$ alkylene.

13. The compound of claim 1, wherein Z is OC(O)N.

14. The compound of claim 1, wherein the compound is a compound of formula (IC):

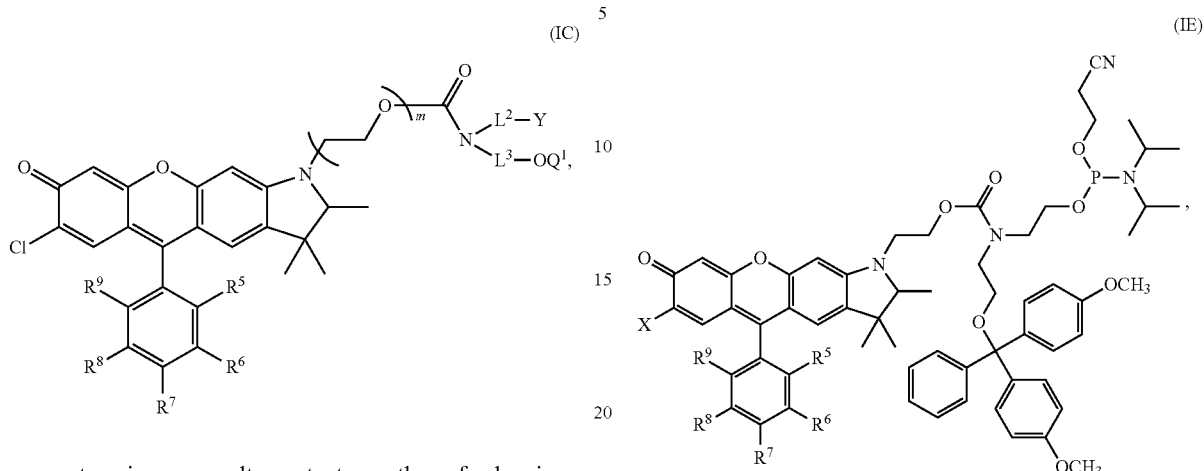

or a stereoisomer, a salt, or a tautomer thereof, wherein m is an integer from 1 to 10.

15. The compound of claim 1, wherein the compound is a compound of formula (ID):

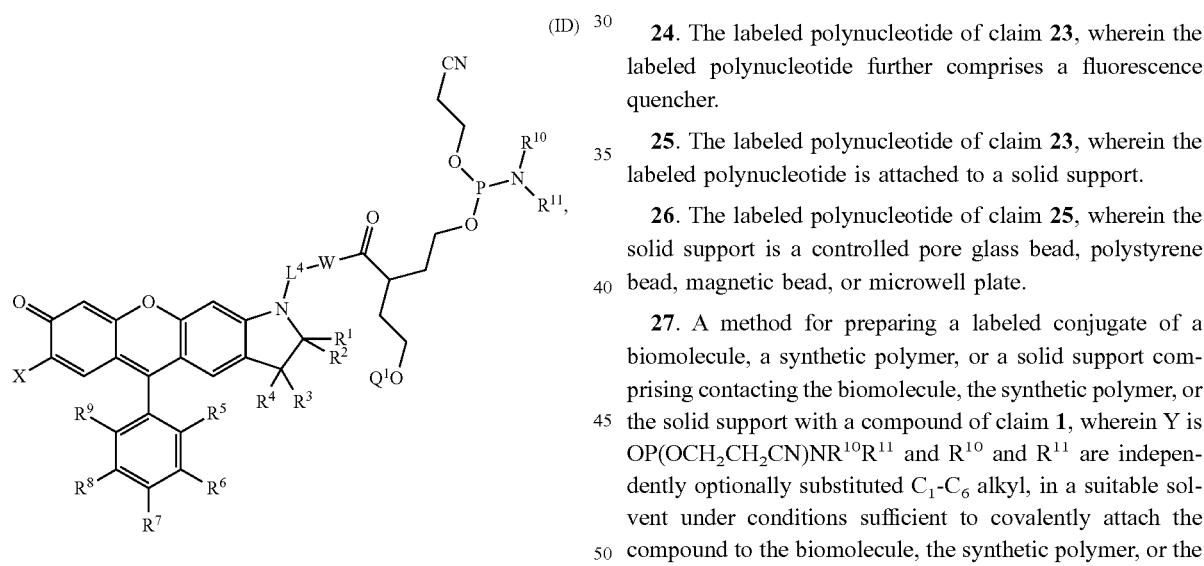

a stereoisomer, a salt, or a tautomer thereof, wherein W is NH or O, and $L^4$ is an substituted $C_2$-$C_{10}$ alkylene or optionally substituted $C_2$-$C_{50}$ heteroalkylene.

16. The compound of claim 1, wherein $Q^1$ is trimethylsilyl, TBDMS, acetyl, trityl, or trityl.

17. The compound of claim 1, wherein $R^{10}$ and $R^{11}$ are isopropyl.

18. The compound of claim 1, wherein $R^5$ is methyl.

19. The compound of claim 1, wherein $R^7$ is methyl.

20. The compound of claim 1, wherein $R^8$ is methyl.

21. The compound of claim 1, wherein $R^6$ and $R^9$ are H.

22. The compound of claim 1, wherein the compound is a compound of formula (IE):

or a stereoisomer, a salt, or a tautomer thereof.

23. A labeled polynucleotide prepared using automated phosphoramidite synthesis formed from the compound of claim 1.

24. The labeled polynucleotide of claim 23, wherein the labeled polynucleotide further comprises a fluorescence quencher.

25. The labeled polynucleotide of claim 23, wherein the labeled polynucleotide is attached to a solid support.

26. The labeled polynucleotide of claim 25, wherein the solid support is a controlled pore glass bead, polystyrene bead, magnetic bead, or microwell plate.

27. A method for preparing a labeled conjugate of a biomolecule, a synthetic polymer, or a solid support comprising contacting the biomolecule, the synthetic polymer, or the solid support with a compound of claim 1, wherein Y is $OP(OCH_2CH_2CN)NR^{10}R^{11}$ and $R^{10}$ and $R^{11}$ are independently optionally substituted $C_1$-$C_6$ alkyl, in a suitable solvent under conditions sufficient to covalently attach the compound to the biomolecule, the synthetic polymer, or the solid support thereby forming the labeled conjugate.

28. The method of claim 27, wherein the solid support is controlled pore glass or polystyrene.

29. The method of claim 27, wherein the biomolecule is a polynucleotide.

30. The method of claim 27, wherein the conditions sufficient to covalently attach the compound to the polynucleotide are automated phosphoramidite oligonucleotide synthesis conditions.

31. An automated molecular diagnostics cartridge comprising the labeled polynucleotide of claim 23.

32. The cartridge of claim 31, wherein the cartridge is a PCR diagnostic cartridge.

33. A compound represented by Formula I:

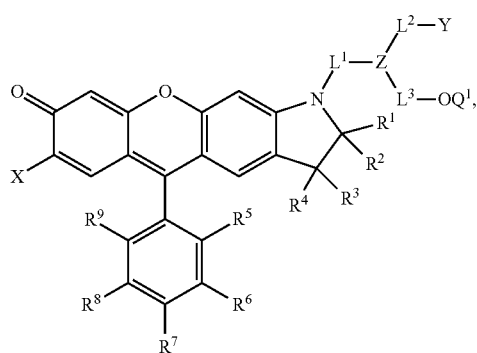

or a stereoisomer, a salt, or a tautomer thereof, wherein:

X is H, halogen, or $C_1$-$C_5$ alkyl;

$R^1$, $R^2$, $R^3$, and $R^4$ are independently H or $C_1$-$C_6$ alkyl;

$R^5$, $R^6$, $R^7$, $R^8$, and $R^9$ are independently H, halogen, or $C_1$-$C_6$ alkyl;

$L^1$ is $C_2$-$C_{10}$ alkylene or $C_2$-$C_{50}$ heteroalkylene;

$L^2$ and $L^3$ are independently $C_2$-$C_{10}$ alkylene or $C_2$-$C_{30}$ heteroalkylene;

$Q^1$ is a hydroxyl protecting group;

Z is CH, N, NHC(O)N, or OC(O)N;

Y is OH, OP(OCH$_2$CH$_2$CN)NR$^{10}$R$^{11}$ or a solid support; and $R^{10}$ and $R^{11}$ are independently $C_1$-$C_6$ alkyl.

34. A labeled polynucleotide prepared using automated phosphoramidite synthesis formed from the compound of claim 33.

35. A method for preparing a labeled conjugate of a biomolecule, a synthetic polymer, or a solid support comprising contacting the biomolecule, the synthetic polymer, or the solid support with a compound of claim 33, wherein Y is OP(OCH$_2$CH$_2$CN)NR$^{10}$R$^{11}$ and $R^{10}$ and $R^{11}$ are independently optionally substituted $C_1$-$C_6$ alkyl, in a suitable solvent under conditions sufficient to covalently attach the compound to the biomolecule, the synthetic polymer, or the solid support thereby forming the labeled conjugate.

36. An automated molecular diagnostics cartridge comprising the labeled polynucleotide of claim 33.

* * * * *